US006822789B2

(12) United States Patent
Kuklinski

(10) Patent No.: US 6,822,789 B2
(45) Date of Patent: *Nov. 23, 2004

(54) OPTICAL ARRAY CONVERTING UV RADIATION

(76) Inventor: Jan Kuklinski, ul. Czarnieckiego 76 m. 1, PL-01-541 Warsaw (PL)

( * ) Notice: Subject to any disclaimer, the term of this patent is extended or adjusted under 35 U.S.C. 154(b) by 0 days.

This patent is subject to a terminal disclaimer.

(21) Appl. No.: 10/151,172

(22) Filed: May 21, 2002

(65) Prior Publication Data

US 2003/0218797 A1 Nov. 27, 2003

Related U.S. Application Data

(63) Continuation-in-part of application No. 09/331,869, filed as application No. PCT/PL97/00033 on Dec. 29, 1997, now Pat. No. 6,392,239.

(30) Foreign Application Priority Data

Dec. 30, 1996 (PL) ................................................ 317746

(51) Int. Cl.[7] ................................................ G02B 5/20
(52) U.S. Cl. ...................... 359/359; 359/350; 359/361; 250/372; 250/252.1
(58) Field of Search ................................ 359/350, 359, 359/361; 250/372, 252.1, 474.1, 226

(56) References Cited

U.S. PATENT DOCUMENTS

| 3,917,948 A | 11/1975 | Strutz ........................ 250/372 |
| 4,010,372 A | 3/1977 | Adler et al. .................. 250/372 |
| 4,086,489 A | 4/1978 | Piltingsrud ................... 250/372 |
| 4,229,733 A | 10/1980 | Tulenko et al. ............... 340/500 |
| 4,428,050 A | 1/1984 | Pellegrino et al. .......... 364/414 |
| 4,535,244 A | 8/1985 | Burnham ..................... 250/372 |
| 4,644,165 A | 2/1987 | Ross et al. .................. 250/372 |
| 4,704,533 A | 11/1987 | Rose et al. .................. 250/342 |
| 4,704,535 A | 11/1987 | Leber et al. ................. 250/372 |
| 4,851,685 A | 7/1989 | Dübgen ........................ 250/372 |
| 4,851,686 A | 7/1989 | Pearson ....................... 250/372 |
| 4,882,598 A | 11/1989 | Wulf ........................ 250/338.1 |
| 4,962,910 A | 10/1990 | Shimizu ..................... 250/372 |
| 4,985,632 A | 1/1991 | Bianco et al. ............... 250/372 |
| 5,008,548 A | 4/1991 | Gat ............................. 250/372 |
| 5,036,311 A | 7/1991 | Moran et al. ................ 340/600 |
| 5,047,131 A | 9/1991 | Wolfe et al. ............ 204/192.23 |
| 5,066,082 A | 11/1991 | Longstaff ..................... 359/361 |
| 5,144,498 A | 9/1992 | Vincent ........................ 359/885 |
| 5,196,705 A | 3/1993 | Ryan ............................ 250/372 |
| 5,306,917 A | 4/1994 | Black et al. ................. 250/372 |
| 5,331,168 A | 7/1994 | Beaubien et al. ........... 250/372 |
| 5,377,045 A | 12/1994 | Wolfe et al. ................. 359/585 |
| 5,401,970 A | 3/1995 | Kinsey et al. .............. 250/372 |
| 5,686,727 A | 11/1997 | Reenstra et al. ............ 250/372 |
| 6,426,503 B1 * | 7/2002 | Wuest ......................... 250/372 |

FOREIGN PATENT DOCUMENTS

| JP | 62-54128 | 3/1987 |
| JP | 64-18028 | 1/1989 |
| SU | 1753302 A1 | 8/1992 |
| WO | WO 98/29715 | 7/1998 |

OTHER PUBLICATIONS

Hoyt S. Scott, "Measurements of Erythemal Energy", Member AIEE General Electric Company, Cleveland, Ohio, May 16, 1949.

* cited by examiner

Primary Examiner—Mark A. Robinson
Assistant Examiner—Lee Fineman
(74) Attorney, Agent, or Firm—Morgan, Lewis & Bockius LLP

(57) ABSTRACT

An optical array containing a system of absorptive filters and a system of interference filters. For the sun light the spectral characteristics of transmission of the optical array is close to the world-wide accepted Diffey Standard. That standard models human skin sensitivity to UV burning. The invention allows making inexpensive, miniature UV sensors that can be applied in a miniature devices measuring burning power of UV contained in the sun light.

10 Claims, 4 Drawing Sheets

OPTICAL ARRAY CONVERTING UV RADIATION

This application claims the benefit under 35 U.S.C. § 120 as a Continuation-in-Part of U.S. application Ser. No. 09/331,869, filed on Sep. 10, 1999, now U.S. Pat. No. 6,392,239 B1 which is a 371 of PCT International Application No. PCT/PL97/00033, filed Dec. 29, 1997.

This invention is an optical array converting ultraviolet (UV) radiation, especially contained in sunlight. The spectral characteristic of the transmission of the filter is similar to the sensitivity of human skin to sun burning. That sensitivity is described by the widely recognized Diffey Standard, also called also the Erythema Action Spectrum.

The Roberston Berger UV meter has been widely used over the past two decades to measure UV in good approximation of the Diffey/Erythemal Spectral Response. This stationary device is based on a phosphore convertor screen as the principle means to reach a spectral response close to the Erythemal/Diffey Curve.

By now there are a few UV hand-held measuring devices known on the market that are targeting monitoring of UV radiation for avoiding sunburning. CASIO Computer Ltd. manufactures a device called "CASIO UC-120 UV", which has an optical array containing absorptive filter made of material similar to Schott UG-11 and a photodiode. The spectral characteristic of the device doesn't match the Diffey Standard. The device illuminated by sunlight is too sensitive to UV-A, that has low burning power.

U.S. Pat. No. 5,196,705 describes a device measuring the intensity and dose of UV. The device has an optical array containing: an absorptive filter made of material similar to Schott UG-11, a photo-luminescentive material and a photodiode. The spectral characteristic of the device doesn't match the Diffey Standard. The device is too sensitive to UV-A comparing to its sensitivity to UV-B. Several others solutions for biologically oriented monitors of UV radiation were also proposed, among them: U.S. Pat. No. 5,036,311 describes a UV-monitoring system in which a light sensing element is placed under a curved optical element with interference filters imposed on its surface.

U.S. Pat. No. 5,401,970 describes a UV-monitoring device which incorporates a UV-B sensor and a VIS sensor. The UV-B detector involved is described to be based on a phosphor convertor screen.

DESCRIPTION OF THE INVENTION

The invention solves the problem of constructing a device equipped with an optical array converting UV, visible and IR radiation that has the spectral characteristic of the transmission similar to the Diffey Standard.

Definition of the relative internal transmission of a set of filters:

$$T^{rel}_{int}(\lambda) = T_{int}(\lambda)/T_{int}(310) \quad (1)$$

where:

$\lambda$ wavelength in nano-meters $T^{rel}_{int}(\lambda)$ relative internal transmission for $\lambda$ wavelength $T_{int}(\lambda)$ internal transmission for $\lambda$ wavelength $T_{int}(310)$ internal transmission for 310 nm wavelength Note that the total internal transmission of the set of absorptive filters is equal to the product of internal transmissions of each consecutive filter.

Definition of the relative transmission of a set of filters:

$$T^{rel}(\lambda) = T(\lambda)/T(310) \quad (2)$$

where:

$\lambda$ wavelength in nano-meters $T^{rel}(\lambda)$ relative transmission for $\lambda$ wavelength $T(\lambda)$ transmission for $\lambda$ wavelength $T(310)$ transmission for 310 nm wavelength $$\text{The Diffey spectral characteristics will be denoted as } D(\lambda) \quad (3)$$

where: $\lambda$ wavelength in nano-meters

In the first solution the array contains a system of absorptive filters to block visible and IR radiation, a system of interference filters modifying transmission of UV and/or blocking visible and IR radiation, scattering elements, elements forming the light beam. Interference filter/filters is/are made of layers of materials having high and low UV refractive indexes. According to the invention one of the system of interference filters has layers made of Hafnium oxide and/or Zirconium oxide. A collimator placed in the optical path forms the light beam. The collimator can have surfaces highly absorbing light. At the beginning of the optical path a scatterer is placed to achieve non-directional characteristic of the array. The scatterer can be made of polytetrafluoroethylene (PTFE).

In another embodiment of the first solution the array contains a system of absorptive filters to block visible and IR radiation, a system of interference filters made of M1 material, modifying transmission of UV and/or blocking visible and IR radiation, scattering elements, elements forming the light beam. This M1 material is characterized by internal transmission for a given wavelength divided by its internal transmission for 310 nm light within the following range: between 0 and 0.7 for $\lambda$=290 nm, between 0.3 and 1.5 for $\lambda$=300 nm, between 0.5 and 2.0 for $\lambda$=320 nm, between 0.5 and 3.0 for $\lambda$=330 nm, between 0.5 and 2.0 for $\lambda$=340 nm, between 0.5 and 1.7 for $\lambda$=350 nm, between 0.1 and 1.5 for $\lambda$=360 nm, between 0.01 and 1.0 for $\lambda$=370 nm, between 10E-5 and 10E-1 for $\lambda$=380 nm, between 10E-12 and 10E-2 for $\lambda$=390 nm. Interference filter/filters is/are made of layers of materials having high and low UV refractive indexes. According to the invention one of the system of interference filters has layers made of Hafnium oxide and/or Zirconium oxide. A collimator placed in the optical path forms the light beam. The collimator can have surfaces highly absorbing light. At the beginning of the optical path a scatterer is placed to achieve non-directional characteristic of the array. The scatterer can be made of PTFE.

In the second solution the array contains the first system of absorptive filters to partly block UV-A, the second system of absorptive filters to block visible and IR radiation and may contain scattering elements and/or system/systems of interference filter/filters. The first system of absorptive filters has internal relative transmission $T^{rel}_{int}(\lambda)$: between 0 and 0.2 for $\lambda$=290 nm, between 0.34 and 0.7 for $\lambda$=300 nm, between 0.5 and 0.8 for $\lambda$=320 nm, between 0.04 and 0.36 for $\lambda$=330 nm, between 10E-3 and 0.1 for $\lambda$=340 nm, between 7*10E-6 and 0.02 for $\lambda$=350 nm, between 2*10E-7 and 7*10E-3 for $\lambda$=360 nm, between 2*10E-7 and 7*10E-3 for $\lambda$=370 nm, between 2*10E-5 and 0.03 for $\lambda$=380 nm, between 2*10E-3 and 0.14 for $\lambda$=390 nm. The total optical thickness of the first system of absorptive filters is between 0.5 and 2 mm.

The second system of absorptive filters has internal relative transmission $T^{rel}_{int}(\lambda)$: between 0 and 0.3 for $\lambda$=290 nm, between 0.7 and 0.8 for $\lambda$=300 nm, between 1 and 1.3 for $\lambda$=320 nm, between 1 and 1.4 for $\lambda$=330 nm, between 1 and 1.3 for $\lambda$=340 nm, between 1 and 1.12 for $\lambda$=350 nm, between 0.6 and 0.8 for $\lambda$=360 nm, between 0.14 and 0.3 for $\lambda$=370 nm, between 10E-3 and 0.015 for $\lambda$=380 nm, between 10E-10 and 10E-6 for $\lambda$=390 nm. The total optical thickness of the first system of absorptive filters is between 0.5 and 10 mm.

At the beginning of the optical path a scatterer is placed to achieve non-directional characteristic of the array. The scatterer can be made of PTFE. In the optical path additional system/systems of interference filters can be placed to block visible and IR radiation and/or to modify transmission in UV range.

In another embodiment of the second solution the internal transmissions are arranged slightly differently. In this embodiment, the array contains the first system of asbsorptive filters to partly block UV-A, the second system of absorptive filters to block visible and IR radiation and may contain scattering elements and/or system/systems of interference filter/filters. The first system of absorptive filters has internal relative transmission $T^{rel}_{int}(\lambda)$: between 0 and 0.6 for $\lambda$=290 nm, between 0.1 and 1.5 for $\lambda$=300 nm, between 0.2 and 2.0 for $\lambda$=320 nm, between 10E-4 and 10E-1 for $\lambda$=330 nm, between 10E-2 and 1.0 for $\lambda$=340 nm, between 10E-8 and 0.1for $\lambda$=350 nm, between 10E-9 and 10E-2 for $\lambda$=360 nm, between 10E-9 and 10E-2 for $\lambda$=370 nm, between 10E-6 and 0.1 for $\lambda$=380 nm, between 10E-4 and 0.1 for $\lambda$=390 nm.

The second system of absorptive filters has internal relative transmission $T^{rel}_{int}(\lambda)$: between 0 and 0.7 for $\lambda$=290 nm, between 0.3 and 1.5 for $\lambda$=300 nm, between 0.5 and 2 for $\lambda$=320 nm, between 0.5 and 3 for $\lambda$=330 nm, between 0.5 and 2 for $\lambda$=340 nm, between 0.5 and 1.7 for $\lambda$=350 nm, between 0.1 and 1.5 for $\lambda$=360 nm, between 0.01 and 1 for $\lambda$=370 nm, between 10E-5 and 10E-1 for $\lambda$=380 nm, between 10E-12 and 10E-2 for $\lambda$=390 nm.

At the beginning of the optical path a scatterer is placed to achieve non-directional characteristic of the array. The scatterer can be made of PTFE. In the optical path additional system/systems of interference filters can be placed to block visible and IR radiation and/or to modify transmission in UV range.

This invention allows producing a cheap and simple optical array with a spectral characteristics in the UV-A and UV-B range following the human skin sensitivity described by Diffey Standard. The scatterer ensures non-directional characteristics of the array. Other standards of skin sensitivity to UV-A and UV-B burning can also be easily followed.

BRIEF DESCRIPTION OF THE DRAWINGS

The invention is presented on the block diagrams where.

DESCRIPTION OF THE VERSION 1

Figure 1:
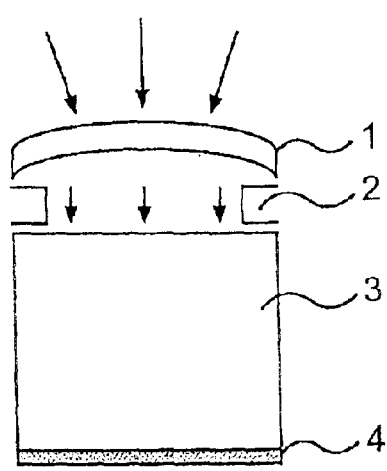
FIG. 1 presents the construction of the version 1 of the optical array.

The array contains: the layer 1 that scatters light, a collimator 2 an absorptive filter 3 that makes a system of absorptive filters, a set of interference filters 4 that makes a system of interference filters. The absorptive filter 3 is made of material transparent to UV and blocking visible and IR radiation. That property has M1 material, with a characteristics presented in the table below.

In that example a scatterer 1 is made of PTFE, and the absorptive filter 3 is a plano-parallel plate, 8 mm thick, made of M1 material Schott UG-11 like. The set of interference filters 4 that is placed on the absorptive filter's 3 surface consists of 38 layers of Hafnium oxide and/or Zirconium oxide and Silicon oxide.

The scatterer 1 ensures non-directional characteristics of the array. The collimator 2 forms the light beam. To achieve desired spectral characteristics the light beam passes through the absorptive filter 3 and the interference filter 4.

Figure 2:
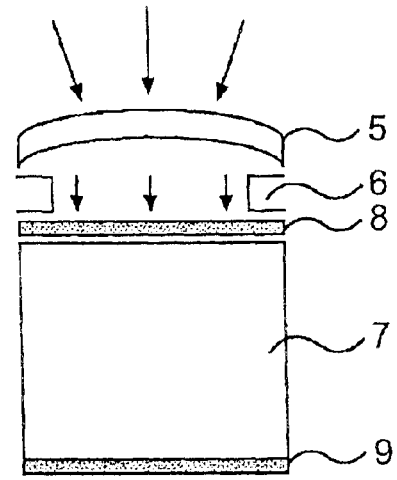
FIG. 2 presents the construction of another variant of the invention presented on FIG. 1.

In the other variant of the version 1, that is shown on the FIG. 2, the array contains: the layer 5 that scatters light, a collimator 6, absorptive filter 7 that makes a system of absorptive filters and a first set of interference filters 8 and a second set of interference filters 9 that both make a system of interference filters. The absorptive filter 7 is made of material transparent to UV and blocking visible and IR radiation. That property has M1 material, with a characteristics presented in the table below.

In that example a scatterer 5 is made of PTFE, and absorptive filter 7 is a plano-parallel plate, 8 mm thick, made of M1 material, Schott UG-11 like. The first set of interference filters 8 and the second set of interference filters 9 are placed on the absorptive filter's 7 surfaces and together consists of 62 layers of Hafnium oxide and/or Zirconium oxide and Silicon oxide.

The scatterer 5 ensures non-directional characteristics of the array. The collimator 6 forms the light beam. To achieve desired spectral characteristics the light beam passes through the first interference filter 8, the absorptive filter 7 and the second interference filter 9.

Figure 5:
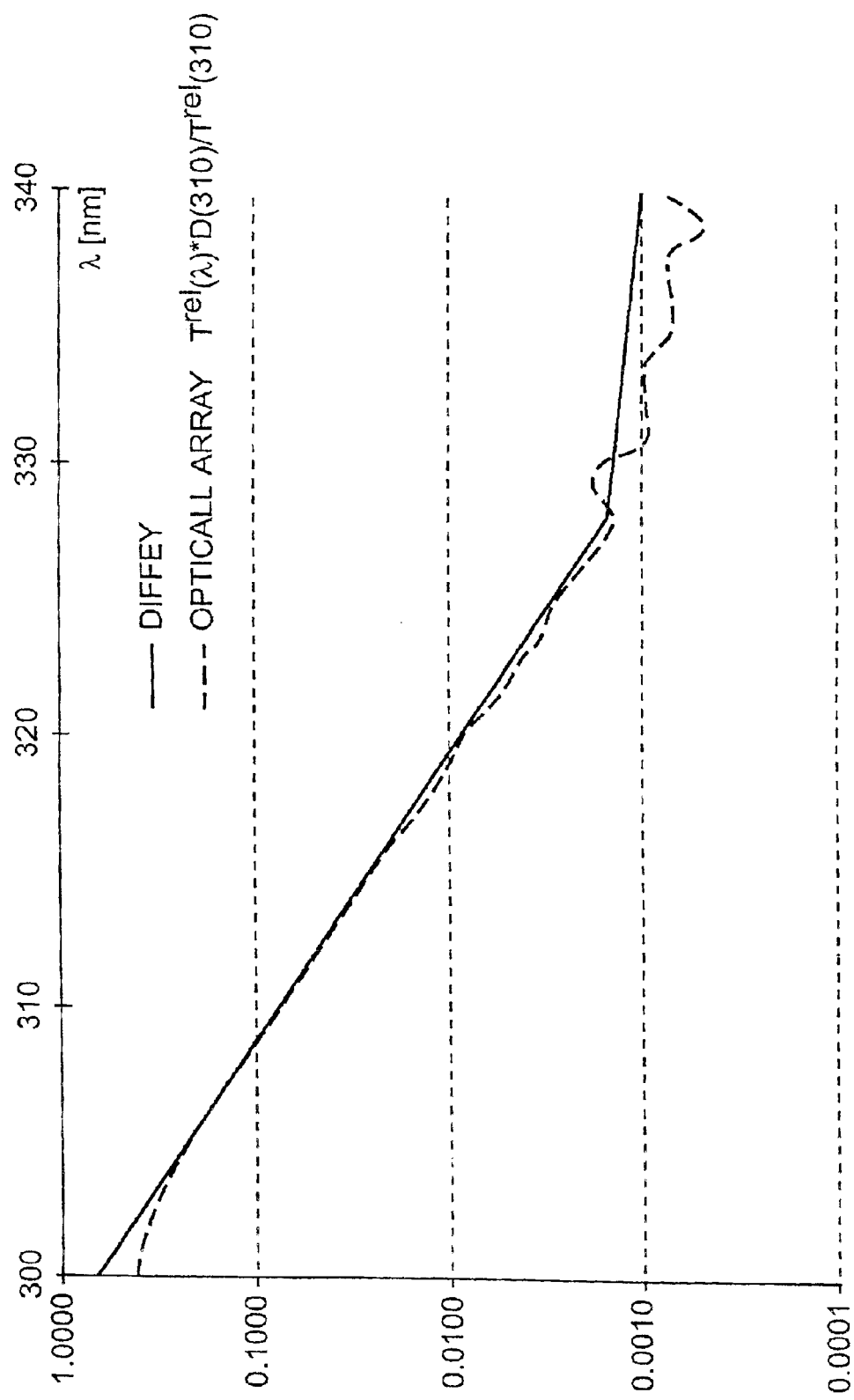
FIG. 5 presents $T^{rel}(\lambda)*D(310)/T^{rel}(310)$ for optical array from FIG. 2 in comparison with the Diffey Standard $D(\lambda)$.

On the FIG. 5 chart the $T^{rel}(\lambda)*D(310)/T^{rel}(310)$ characteristics of the array is plotted as a broken line, the Diffey Standard is plotted as a solid line. On the chart these two curves are close to each other in the 310–325 nm range.

DESCRIPTION OF THE VERSION 2

The array contains: the layer 10 that scatters light, a first absorptive filter 11 that makes a first system of absorptive filters, a second absorptive filter 12 that makes a second system of absorptive filters. The first absorptive filter 11 is made of material transparent to UV with decreasing transmission when the wavelength is changed from 320 to 350 nm, the second absorptive filter 12 is made of material transparent to UV and blocking visible and IR radiation. That property have materials M2 and M1 respectively, with characteristics presented in the table below.

In that example a scatterer 10 is made of PTFE, the first absorptive filter 11 is a plano-parallel plate, 1.5 mm thick, made of M2 1 material, Schott GG-19 like, the second absorptive filter 12 is a plano-parallel plate, 8 mm thick, made of M1 material, Schott UG-11 like.

The scatterer 10 ensures non-directional characteristics of the array. To achieve desired spectral characteristics the light beam passes through the first absorptive filter 11 and the second absorptive filter 12.

Figure 6:
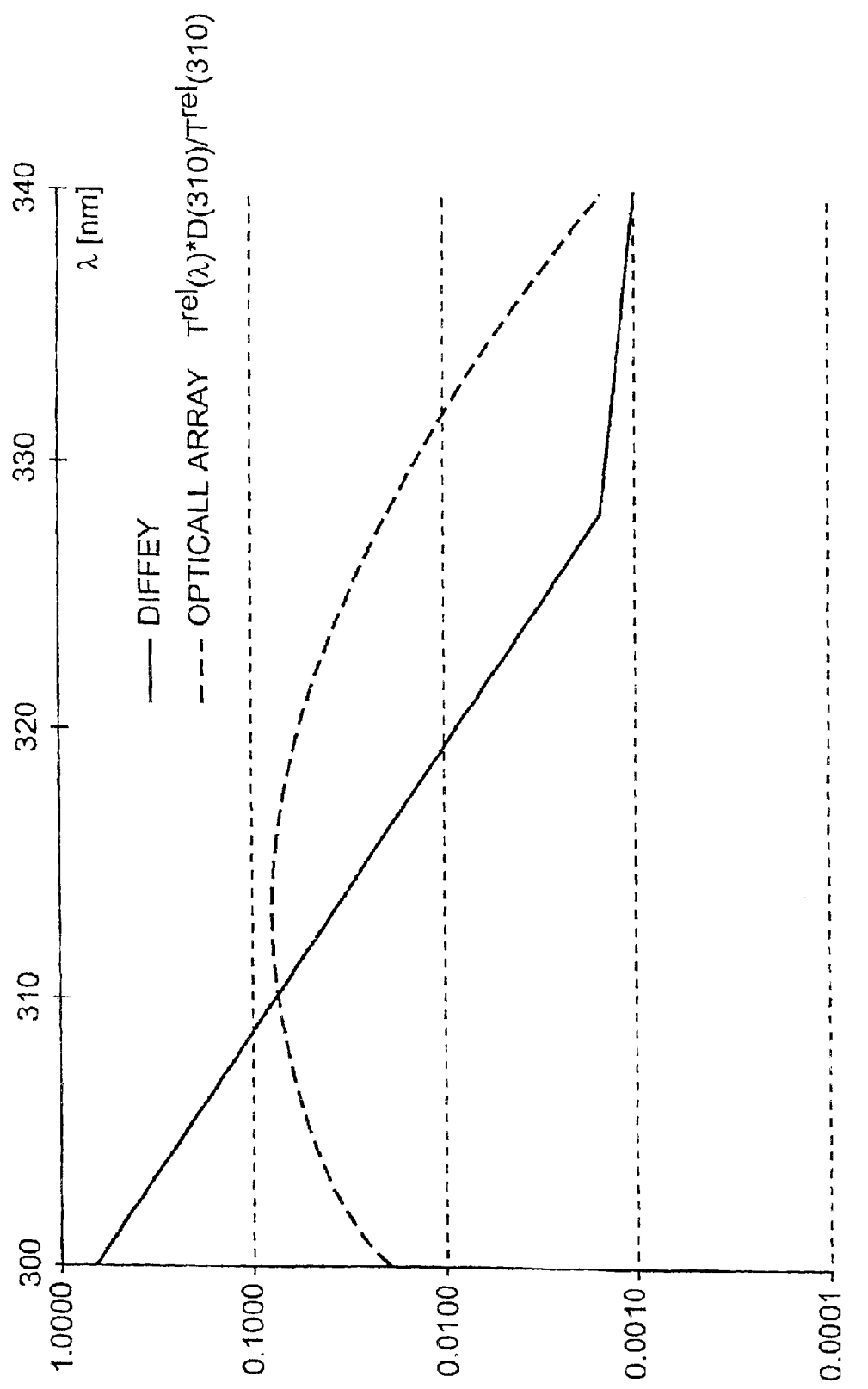
FIG. 6 presents $T^{rel}(\lambda)*D(310)/T^{rel}(310)$ for optical array from FIG. 3 in comparison with the Diffey Standard $D(\lambda)$.

On the FIG. 6 chart $T^{rel}(\lambda)*D(310)/T^{rel}(310)$ characteristics of the array is plotted as a broken line, the Diffey Standard is plotted as a solid line.

DESCRIPTION OF THE VERSION 3

The array contains: a first absorptive filter 13 that makes a first system of absorptive filters, a second absorptive filter 14 that makes a second system of absorptive filters and a first set of interference filters 15 and a second set of interference filters 16 that both make a system of interference filters. The first absorptive filter 13 is made of material transparent to UV with decreasing transmission when wavelength is changed from 320 to 350 nm, the second absorptive filter 14 is made of material transparent to UV and blocking visible and IR radiation. That property have materials M2 and M1 respectively, with characteristics presented in the table below. Interference filters are constructed to block visible and IR radiation and/or to modify transmission characteristics in UV.

In that example the first absorptive filter 13 is a planoparallel plate, 1.5 mm thick, made of M2 material, Schott GG-19 like. The second absorptive filter 14 with interference filters 15, 16 placed on the filter 14 surfaces are made together by Schott as Schott DUG-11 filter.

To achieve desired spectral characteristics the light beam passes through the first absorptive filter 13, the first interference filter 15, the second absorptive filter 14 and the second interference filter 16.

Figure 7:
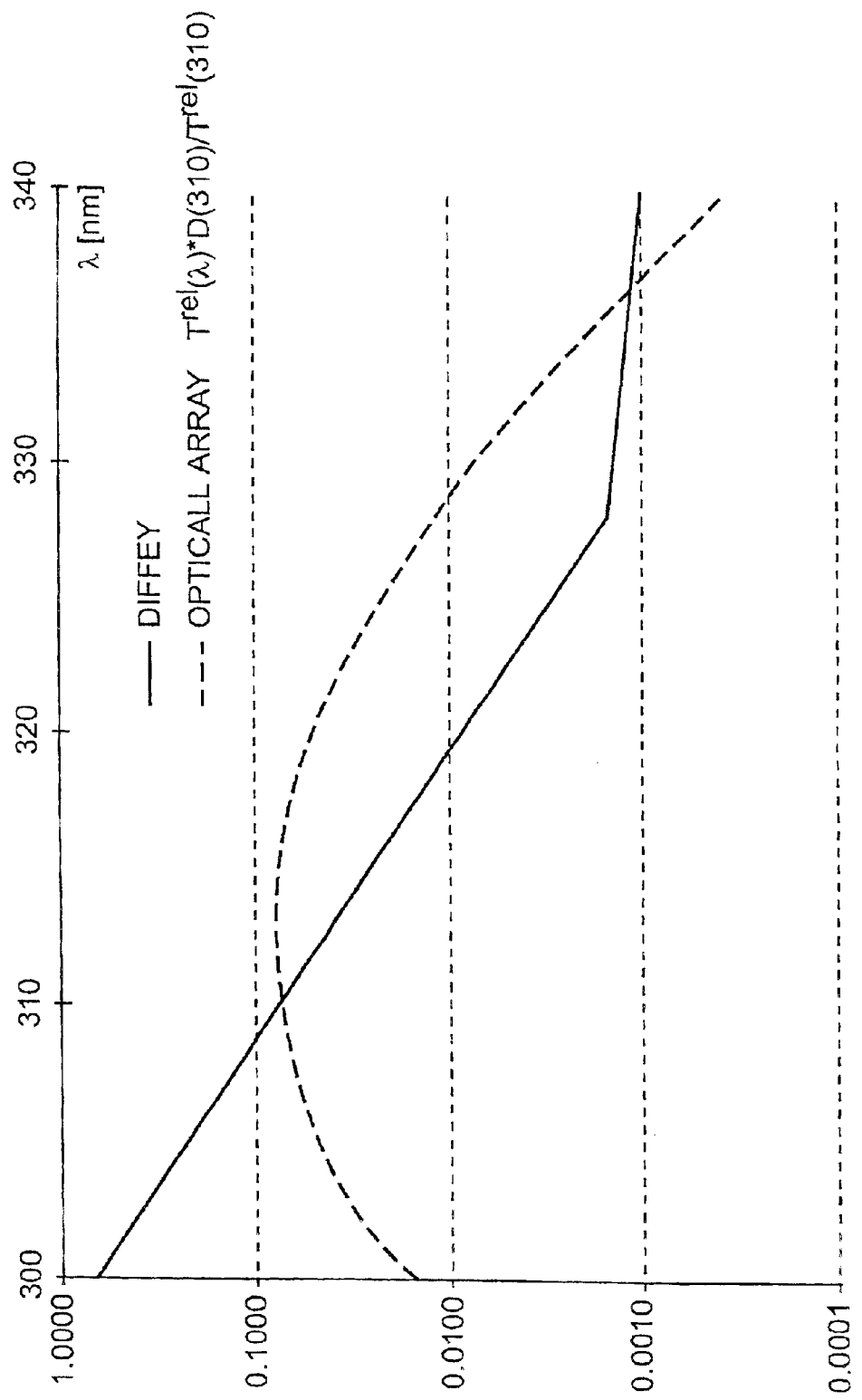
FIG. 7 presents $T^{rel}(\lambda)*D(310)/T^{rel}(310)$ for optical array from FIG. 4 in comparison with the Diffey Standard $D(\lambda)$.

On the FIG. 7 chart $T^{rel}(\lambda)*D(310)/T^{rel}(310)$ characteristics of the array is plotted as a broken line, the Diffey Standard is plotted as a solid line.

TABLE of relative internal transmission $T_{int}^{rel}(\lambda)$

| λ[nm] | | 290 | 300 | 310 | 320 | 330 | 340 | 350 | 360 | 370 | 380 | 390 |
|---|---|---|---|---|---|---|---|---|---|---|---|---|
| M1 glass, | Minimal value | 0 | 0.7 | 1 | 1.0 | 1.0 | 1.0 | 1.0 | 0.6 | 0.14 | 10E−3 | 10E−10 |
| 8 mm thick | Maximal value | 0.3 | 0.8 | 1 | 1.3 | 1.4 | 1.3 | 1.12 | 0.8 | 0.3 | 0.015 | 10E−6 |
| M2 glass, | Minimal value | 0 | 0.34 | 1 | 0.5 | 0.04 | 10E−3 | 7*10E−6 | 2*10E−7 | 2*10E−7 | 2*10E−5 | 2*10E−3 |
| 1.5 mm thick | Maximal value | 0.2 | 0.7 | 1 | 0.8 | 0.36 | 0.1 | 0.02 | | 7*10E−3 | 7*10E−3 | 0.03 | 0.14 |

Data in tables above are $T^{rel}_{int}(\lambda)$ characteristics of planoparallel plates made of M1, M2 with given thickness.

Figure 3:
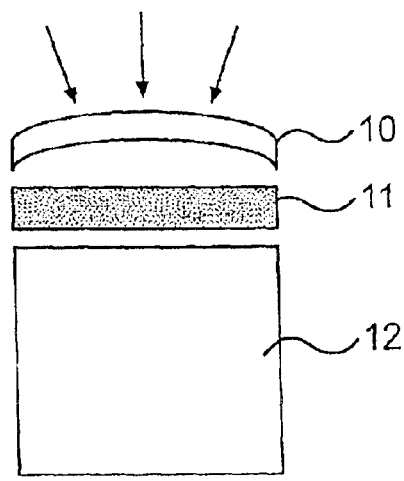
FIG. 3 presents the construction of the version 2 of the optical array.
Figure 4:
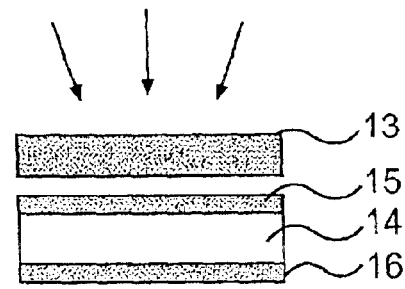
FIG. 4 presents the construction of the of the version 3 of the optical array.

The exact values of $T^{rel}_{int}(\lambda)$ are described in the example constructions. These data are example values and it is obvious that the invention is not restricted to them. The optical array in the example constructions has the spectral characteristics similar to human skin sensitivity to UV contained in sunlight. FIG. 5 presents $T^{rel}(\lambda)*D(310)/T^{rel}(310)$ chart for optical array from FIG. 2 in comparison with the Diffey Standard D(λ), FIG. 6 presents $T^{rel}(\lambda)*D(310)/T^{rel}(310)$ chart for optical array from FIG. 3 in comparison with the Diffey Standard D(λ), FIG. 7 presents $T^{rel}(\lambda)*D(310)/T^{rel}(310)$ chart for optical array from FIG. 4 in comparison with the Diffey Standard D(λ). The biggest discrepancies between the characteristics and the Diffey Standard are for UV-C that is absent in sunlight and UV-A that has a minimal burning power comparing with total burning power of sun UV.

What is claimed is:

1. An optical array converting UV, visible and IR radiation, especially contained in sunlight, comprising:
   a system of absorptive filters, made of M1 material, to modify transmission characteristics, this M1 material is characterized by internal transmission for a given wavelength divided by its internal transmission for 310 nm light within the following range: between 0 and 0.7 for λ=290 nm, between 0.3 and 1.5 for λ=300 nm, between 0.5 and 2.0 for λ=320 nm, between 0.5 and 3.0 for λ=330 nm, between 0.5 and 2.0 for λ=340 nm, between 0.5 and 1.7 for λ=350 nm, between 0.1 and 1.5 for λ=360 nm, between 0.01 and 1.0 for λ=370 nm, between 10E-5 and 10E-1 for λ=380 nm, between 10E-12 and 10E-2 for λ=390 nm;
   a system of interference filters to modify transmission characteristics; and
   a scatterer at the beginning of the optical path to achieve non-directional spectral transmission characteristics of the array and to improve the spectral transmission characteristics of the array.

2. The array in claim 1, further comprising a collimator placed in the optical path to form the light beam passing through the array and to improve the spectral transmission characteristics of the array where a collimator surface is highly absorptive to the light.

3. An optical array converting UV, visible and IR radiation, especially contained in sunlight, comprising:
   a first system of absorptive filters, made of M2 material, to modify transmission characteristics, this M2 material is characterized by internal transmission for a given wavelength divided by its internal transmission for 310 nm light within the following range: between 0 and 0.6 for λ=290 nm, between 0.1 and 1.5 for λ=300 nm, between 0.2 and 2.0 for λ=320 nm, between 10E-4 and 10E-1 for λ=330 nm, between 10E-2 and 1.0 for λ=340 nm, between 10E-8 and 0.1 for λ=350 nm, between 10E-9 and 10E-2 for λ=360 nm, between 10E-9 and 10E-2 for λ=370 nm, between 10E-6 and 0.1 for λ=380 nm, between 10E-4 and 0.1 for λ=390 nm; and
   a second system of absorptive filters, made of M1 material, to modify transmission characteristics, this M1 material is characterized by internal transmission for a given wavelength divided by its internal transmission for 310 nm light within the following range: between 0 and 0.7 for λ=290 nm, between 0.3 and 1.5 for λ=300 nm, between 0.5 and 2.0 for λ=320 nm, between 0.5 and 3.0 for λ=330 nm, between 0.5 and 2.0 for λ=340 nm, between 0.5 and 1.7 for λ=350 nm, between 0.1 and 1.5 for λ=360 nm, between 0.01 and 1.0 for λ=370 nm, between 10E-5 and 10E-1 for λ=380 nm, between 10E-12 and 10E-2 for λ=390 nm.

4. The array in claim 3, further comprising a scatter at the beginning of the optical path to achieve non-directional spectral transmission characteristics of the array and to improve the spectral transmission characteristics of the array.

5. The array in claim 3, further comprising additional interference filters to improve the spectral transmission characteristics of the array.

6. An optical array converting UV, visible and IR radiation, especially contained in sunlight, comprising:
   a system of absorptive filters, made of M1 material, to modify transmission characteristics, this M1 material is characterized by internal transmission for a given wavelength divided by its internal transmission for 310 nm light within the following range: between 0 and 0.3 for λ=290nm, between 0.7 and 0.8 for λ=300 nm, between 1 and 1.3 for λ=320 nm, between 1 and 1.4 for λ=330 nm, between 1 and 1.3 for λ=340 nm, between 1 and 1.12 for λ=350 nm, between 0.6 and 0.8 for λ=360 nm, between 0.14 and 0.3 for λ=370 nm, between 10E-3 and 0.015 for λ=380 nm, between 10E-10 and 10E-6 for λ=390 nm;

a system of interference filters to modify transmission characteristics; and a scatterer at the beginning of the optical path to achieve non-directional spectral transmission characteristics of the array and to improve the spectral transmission characteristics of the array.

7. The array in claim 6, further comprising a collimator placed in the optical path to form the light beam passing through the array and to improve the spectral transmission characteristics of the array where a collimator surface is highly absorptive to the light.

8. An optical array converting UV, visible and IR radiation, especially contained in sunlight, comprising:

a first system of absorptive filters, made of M2 material, to modify transmission characteristics, this M2 material is characterized by internal transmission for a given wavelength divided by its internal transmission for 310 nm light within the following range: between 0 and 0.2 for λ=290 nm, between 0.34 ad 0.7 for λ=300 nm, between 0.5 and 0.8 for λ=320 nm, between 0.04 and 0.36 for λ=330 nm, between 10E-3 and 0.1 for λ=340 nm, between 7*10E-6 and 0.02 for λ=350nm, between 2*10E-7 and 7*10E-3 for λ=360 nm, between 2*10E-7 and 7*10E-3 for λ=370 nm, between 2*10E-5 and 0.03 for λ=380 nm, between 2*10E-3 and 0.14 for λ=390 nm; and a second system of absorptive filters, made of M1 material, to modify transmission characteristics, this M1 material is characterized by internal transmission for a given wavelength divided by its internal transmission for 310 nm light within the following range: between 0 and 0.3 for λ=290 nm, between 0.7 and 0.8 for λ=300 nm, between 1 and 1.3 for λ=320 nm, between 1 and 1.4 for λ=330 nm, between 1 and 1.3 for λ=340 nm, between 1 and 1.12 for λ=350 nm, between 0.6 and 0.8 for λ=360 nm, between 0.14 and 0.3 for λ=370 nm, between 10E-3 and 0.015 for λ=380 nm, between 10E-10 and 10E-6 for λ=390 nm.

9. The array in claim 8, further comprising a scatterer at the beginning of the optical path to achieve non-directional spectral transmission characteristics of the array and to improve the spectral transmission characteristics of the array.

10. The array in claim 8, further comprising additional interference filters to improve the spectral transmission characteristics of the array.

* * * * *